US012791177B2

(12) United States Patent
Shen

(10) Patent No.: US 12,791,177 B2
(45) Date of Patent: Nov. 10, 2026

(54) WATER IMMERSIVE ELECTRIC SHOCK PROTECTION FOR AN ULTRAVIOLET SANITATION SYSTEM

(71) Applicant: Wonder UV Purification (M) SDN. BHD, Bahru (MY)

(72) Inventor: Kui Shen, ZhongShan (CN)

(73) Assignee: WONDER UV PURIFICATION (M) SDN. BHD, Bahru (MY)

( * ) Notice: Subject to any disclaimer, the term of this patent is extended or adjusted under 35 U.S.C. 154(b) by 328 days.

(21) Appl. No.: 18/638,217

(22) Filed: Apr. 17, 2024

(65) Prior Publication Data

US 2025/0327564 A1 Oct. 23, 2025

(51) Int. Cl.
*A61L 2/10* (2026.01)
*F21V 23/00* (2015.01)
(Continued)

(52) U.S. Cl.
CPC ............ *F21V 23/0471* (2013.01); *A61L 2/10* (2013.01); *F21V 23/003* (2013.01); *F21V 23/06* (2013.01)

(58) Field of Classification Search
CPC ............. F21V 25/00; F21V 23/06; A61L 2/10
See application file for complete search history.

(56) References Cited

FOREIGN PATENT DOCUMENTS

CN 1337922 * 2/2022

OTHER PUBLICATIONS

European Search Opinion EP4636917. Aug. 25, 2025 (Year: 2025).*
Kozlowski. CN1337922. English machine translation. (Year: 2002).*

* cited by examiner

*Primary Examiner* — Donald R Spamer
(74) *Attorney, Agent, or Firm* — CANTOR COLBURN LLP

(57) ABSTRACT

A water immersive electric shock protection apparatus for an ultraviolet (UV) sanitation system and an electrical circuit arrangement for operating same, the apparatus including a lamp base having a proximal end configured to be mounted to a tube of a UV lamp and a distal end having a plurality of connecting pins extending therefrom, the plurality of connecting pins arranged to deliver electrical power to the UV lamp, a lamp socket having a plurality of connecting holes corresponding to the plurality of connecting pins and configured to receive said connecting pins, a first electrical circuit disposed in communication with the plurality of connecting holes and extending to and connectable with an electrical power source, the first electrical circuit arranged to deliver electrical power from the power source to the plurality of connecting pins when received in the corresponding plurality of connecting holes and when the electrical power source is turned on, a detecting pin extending from the distal end of the lamp socket and including an exposed portion, a detecting hole formed in the lamp socket, configured to receive the detecting pin when the plurality of connecting holes said receive the plurality of connecting pins, a second electrical circuit disposed in communication with the detecting hole which receives a leakage signal from the first electrical circuit when the exposed portion of the detecting pin is exposed to a sufficient volume of a conductive substance, and a detecting device connected to the second electrical circuit and configured to detect the leakage signal, to compare the leakage signal to a predetermined set value, and to turn off the electrical power source when the leakage signal exceeds the predetermined set value.

7 Claims, 7 Drawing Sheets

(51) Int. Cl.

| | |
|---|---|
| ***F21V 23/04*** | (2006.01) |
| ***F21V 23/06*** | (2006.01) |

WATER IMMERSIVE ELECTRIC SHOCK PROTECTION FOR AN ULTRAVIOLET SANITATION SYSTEM

TECHNICAL FIELD

This disclosure concerns electrical powered water sanitation systems that utilize ultraviolet (UV) light for disinfection purposes and, more particularly, the disclosure relates to an apparatus, system and method for detecting electricity leaked from related UV sanitation devices due to the presence of water and for disabling the respective devices upon such detection.

BACKGROUND

UV water sanitizers sanitize water by exposing the water to UV light for a prescribed period of time. A typical UV sanitizer includes a stainless steel chamber having a water inlet, a water outlet, and an end opening which receives a quartz sleeve that is sealed against an internal surface of the chamber in a watertight fashion by an o-ring. A first end of a UV lamp is inserted into the quartz sleeve so as to reside within the stainless steel chamber. A second end of the UV lamp is fitted with a lamp base which connects to a lamp socket which is in turn connected to a power source which delivers electrical power to the lamp in order to generate the required UV light.

FIG. 1 illustrates a traditional UV lamp 1 having a lamp tube 2 and a lamp base 3 with pins 4 extending therefrom. FIG. 1 further shows a traditional lamp socket 5 having holes 6 for receiving the pins 4, and a cable 7 for connecting the socket 5 to a ballast.

In order to prevent electric shock and to maintain proper operation of the UV water sanitizer, the connection of the lamp base 3 and lamp socket 5 must be kept isolated from the water passing through the stainless steel chamber and also from ambient water or other fluid which may be present at the exterior of the UV water sanitizer. Traditionally, this hermetic isolation is attempted by disposing the o-ring in a secure fit between the quartz sleeve and the interior of the stainless steel chamber, and by also a waterproof strainer element which is fitted at the end opening of the stainless steel chamber and over the cable.

However, the quartz sleeve is quite fragile and is subject to breakage which would thus expose the lamp to water. Additionally, over prolonged periods of usage, the o-ring can dislodge or the material forming the ring can degrade, in either case, rendering the o-ring permeable to water. Moreover, UV sterilization equipment is widely used in sewage treatment systems. Often, to improve the efficiency of disinfection and sterilization, the equipment is disposed directly in the sewage and is thus surrounded by fluid. The external waterproofing properties of the strainer element arranged over the connected lamp base and lamp socket deteriorate with aging of the equipment. In similar fashion, the reciprocating cycle of thermal expansion and cold contraction, will steadily destroy the watertightness of the assembly.

Thus, through normal usage, there is a risk of the electrical current flowing through the UV lamp to be exposed to water. This poses a significant electrical shock risk to an person who contacts the UV sanitizer, the water flowing therethrough, and the water or sewage in which the sanitizer may be disposed. Unfortunately, existing systems prone to such water exposure and electrical leakage are not capable of detecting such and thus can pose a hidden danger to users, operators, and the general public.

A UV water sanitizer system is needed which can detect water exposure and electrical leakage and take prescriptive steps to ensure safety.

BRIEF SUMMARY

The disclosure provides exemplary embodiments of a water immersive electric shock protection apparatus for an ultraviolet (UV) sanitation system and an electrical circuit arrangement for operating same. In one configuration, the apparatus includes a lamp base having a proximal end configured to be mounted to a tube of a UV lamp and a distal end having a plurality of connecting pins extending therefrom, the plurality of connecting pins arranged to deliver electrical power to the UV lamp, a lamp socket having a plurality of connecting holes corresponding to the plurality of connecting pins and configured to receive said connecting pins, a first electrical circuit disposed in communication with the plurality of connecting holes and extending to and connectable with an electrical power source, the first electrical circuit arranged to deliver electrical power from the power source to the plurality of connecting pins when received in the corresponding plurality of connecting holes and when the electrical power source is turned on, a detecting pin extending from the distal end of the lamp socket and including an exposed portion, a detecting hole formed in the lamp socket, configured to receive the detecting pin when the plurality of connecting holes said receive the plurality of connecting pins, a second electrical circuit disposed in communication with the detecting hole which receives a leakage signal from the first electrical circuit when the exposed portion of the detecting pin is exposed to a sufficient volume of a conductive substance, and a detecting device connected to the second electrical circuit and configured to detect the leakage signal, to compare the leakage signal to a predetermined set value, and to turn off the electrical power source when the leakage signal exceeds the predetermined set value.

The apparatus and corresponding circuitry allow for the operation of a UV sanitation system while simultaneously monitoring the system for electrical leakage which may present a threat to the continued operation of the system and/or to the health and safety of operators, and to terminate electrical power to the UV system when the leakage exceeds a predetermined threshold.

BRIEF DESCRIPTION OF THE DRAWINGS

For a more complete understanding of this disclosure, reference is now made to the following brief description, taken in connection with the accompanying drawings and detailed description, wherein like reference numerals represent like parts, in which.

DETAILED DESCRIPTION

Figure 1:
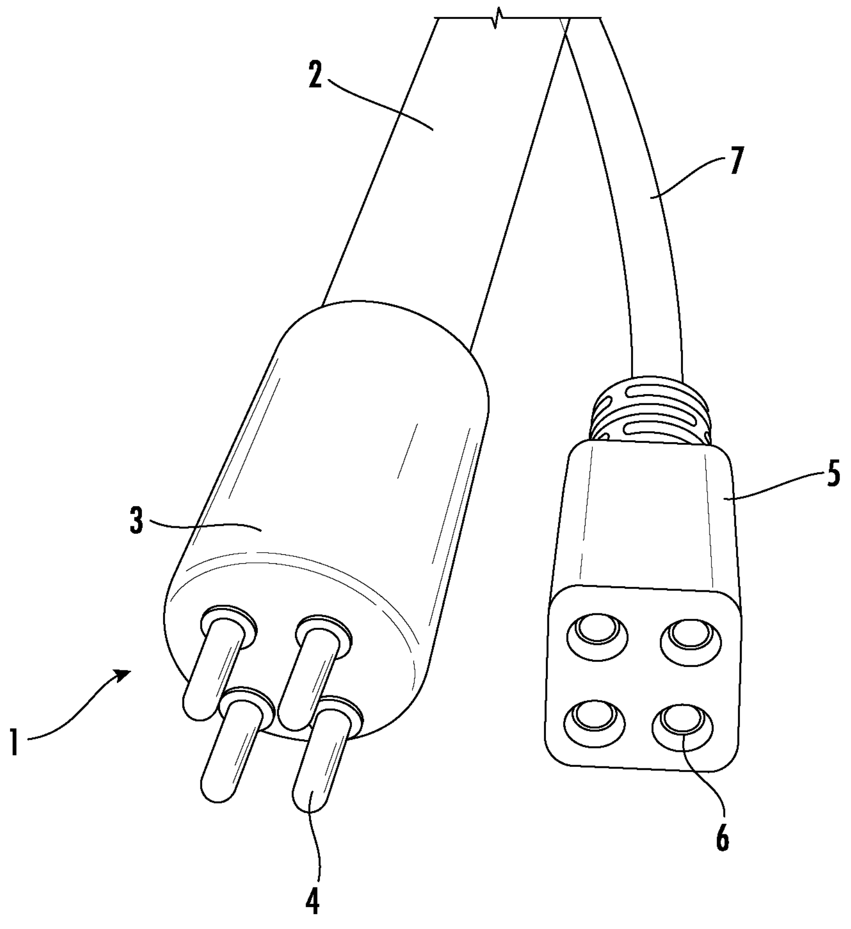
FIG. 1 Prior Art
FIG. 1 shows a traditional UV lamp and lamp socket.
Figure 2:
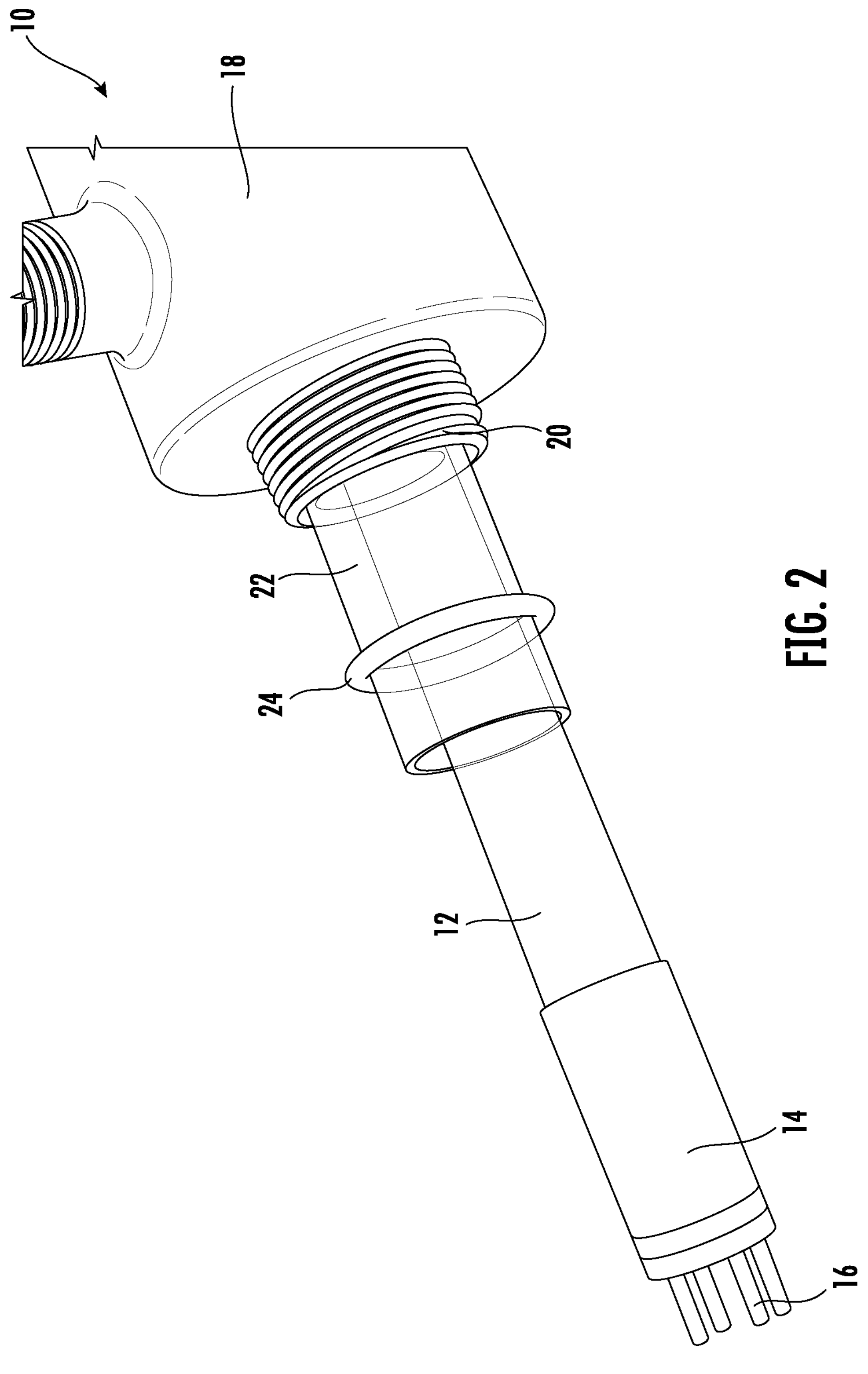
FIG. 2 shows a UV lamp in an exemplary embodiment of the invention.

FIG. 2 shows a UV lamp 10 having a tube 12 and a lamp base 14 affixed to one end of the lamp tube 12. The lamp base 14 has a plurality of connecting pins 16 extending therefrom. The connecting pins 16 deliver power to the UV lamp 10 in the form of electricity when the lamp 10 is connected to a power source. As illustrated, the UV lamp 10 is a component of a UV sanitation system that further includes a stainless steel chamber 18 having an opening 20 at one end thereof for receiving a quartz sleeve 22 into an interior of the chamber 18. An o-ring 24 is used to seal the quartz sleeve 22 against the interior of the chamber 18, and the UV lamp 10 is fitted within the quartz sleeve 22.

Figure 3:
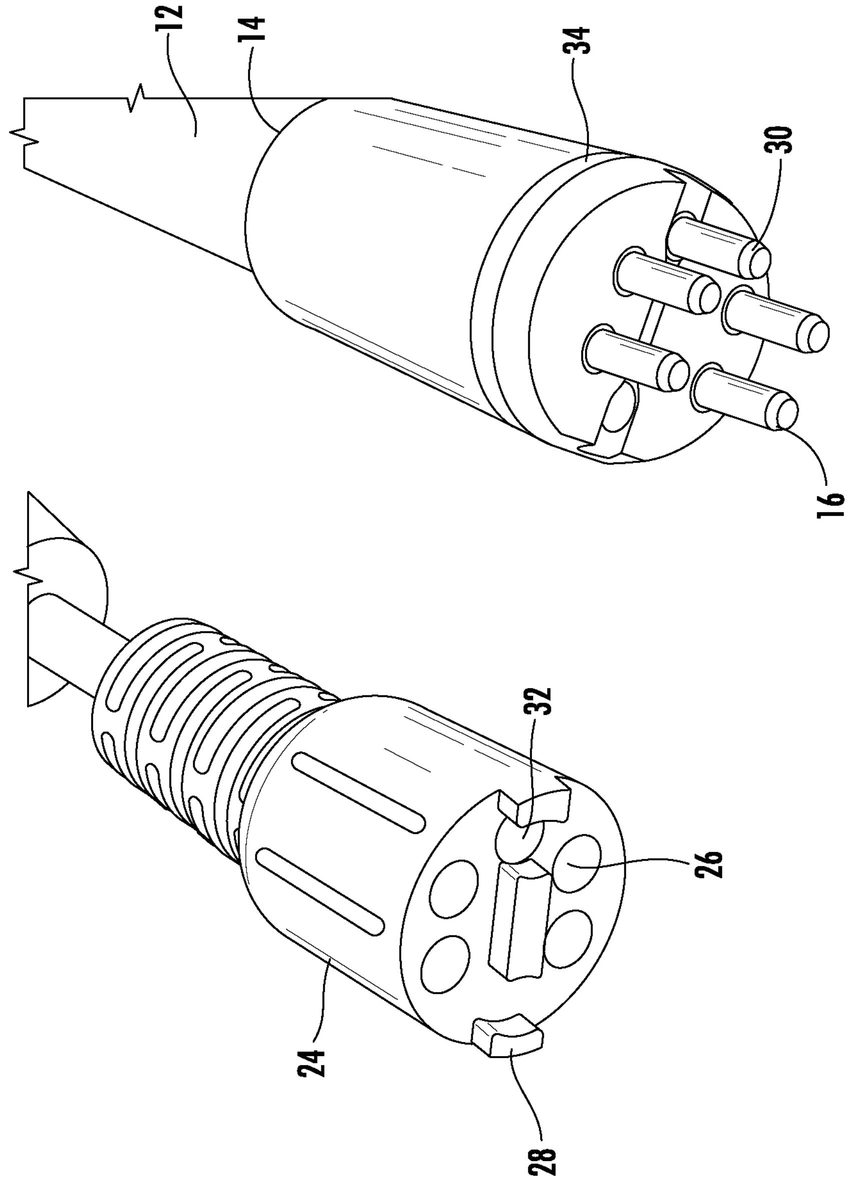
FIG. 3 shows an enlarged view of a lamp base and a lamp socket.
Figure 4:
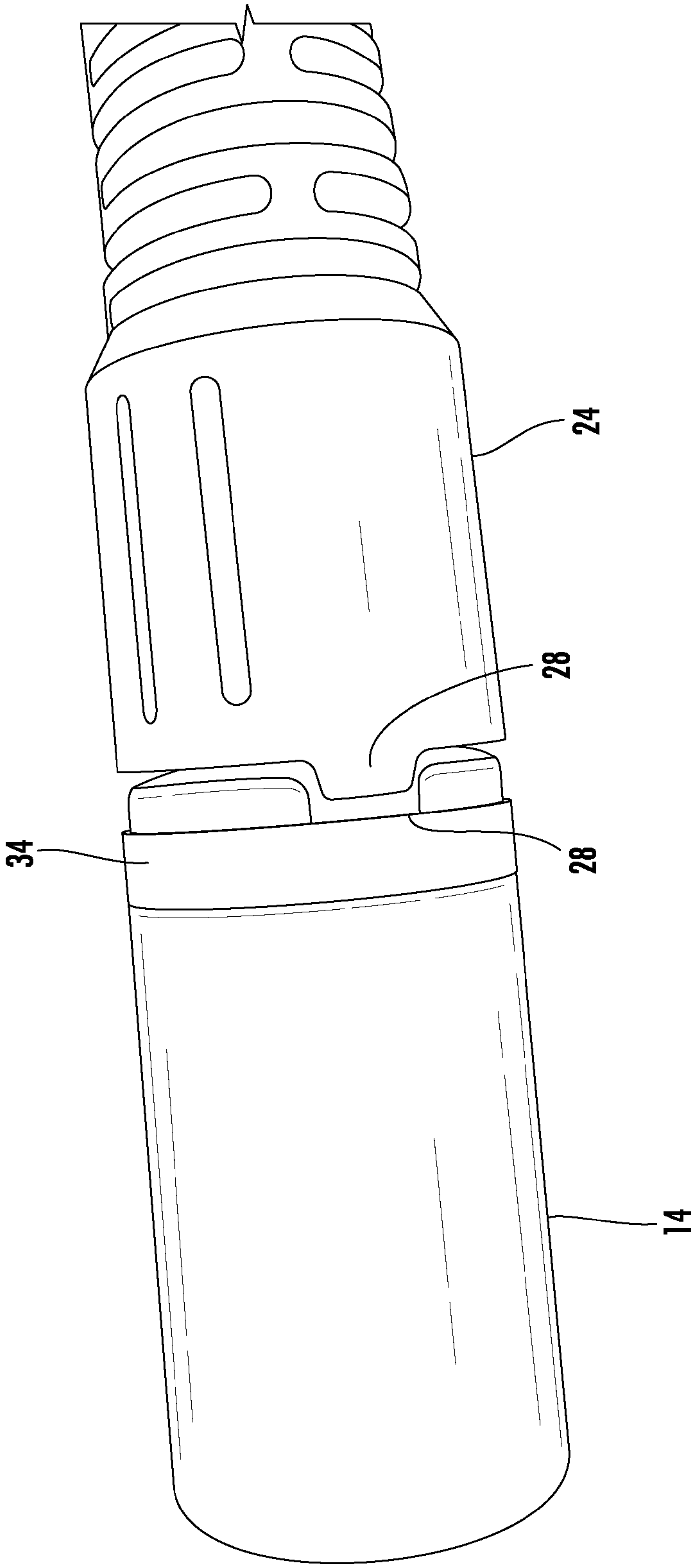
FIG. 4 shows a lamp base and a lamp socket in a mated configuration.

FIG. 3 shows an enlarged view of the UV lamp 10 of FIG. 2, and particularly, the lamp base 14. In this exemplary embodiment, four connecting pins 16 extend from the lamp base 14. FIG. 3 also shows an exemplary embodiment of a lamp socket 24 which is configured to mate with the lamp base 14. This illustrative lamp socket 24 is shown to include four connecting holes 26 which correspond to the four connecting pins 16 of the lamp base 14. When the lamp base 14 and the lamp socket 24 are mated, the four connecting pins 16 are received within the four holes 26. The lamp base 14 and/or the lamp socket 16 may include additional indexing and/or alignment features 28 for facilitating and ensuring the mating of these two components. FIG. 4 shows the lamp base 14 and the lamp socket 24 in a mated configuration with the connecting pins 16 fully received within the connecting holes 26 and the indexing and/or alignment features 28 engaged. In this mated configuration, electricity may flow from the lamp socket 24 to the lamp base 14 in order to power the UV lamp 10, as will be discussed in further detail below.

Returning to FIG. 3, the lamp base 14 further includes a detecting pin 30 protruding therefrom. In the illustrated embodiment, the detecting pin 30 is adjacent to and parallel with the four connecting pins 16. The lamp socket 24 correspondingly includes a detecting hole 32 which is configured to receive the detecting pin 30 when the lamp base 14 and the lamp socket 24 are placed into the mated configuration. The detecting pin 30 includes an exposed portion 34 which is disposed on an exterior surface of the lamp base 14 in one or more areas which may be subjected to water, moisture, or some other conductive fluid or substance. In the illustrated example, the exposed portion 34 extends around a circumference of the lamp base 14 and across a diameter of the end of the lamp base 14 so as to bisect the four connecting pins 16 and to connect the detecting pin 30. As will be discussed in detail herein, the detecting pin 30 and the exposed portion 34 are used to detect the presence of water or moisture in contact with the mated lamp base 14 and lamp socket 24.

Figure 5:
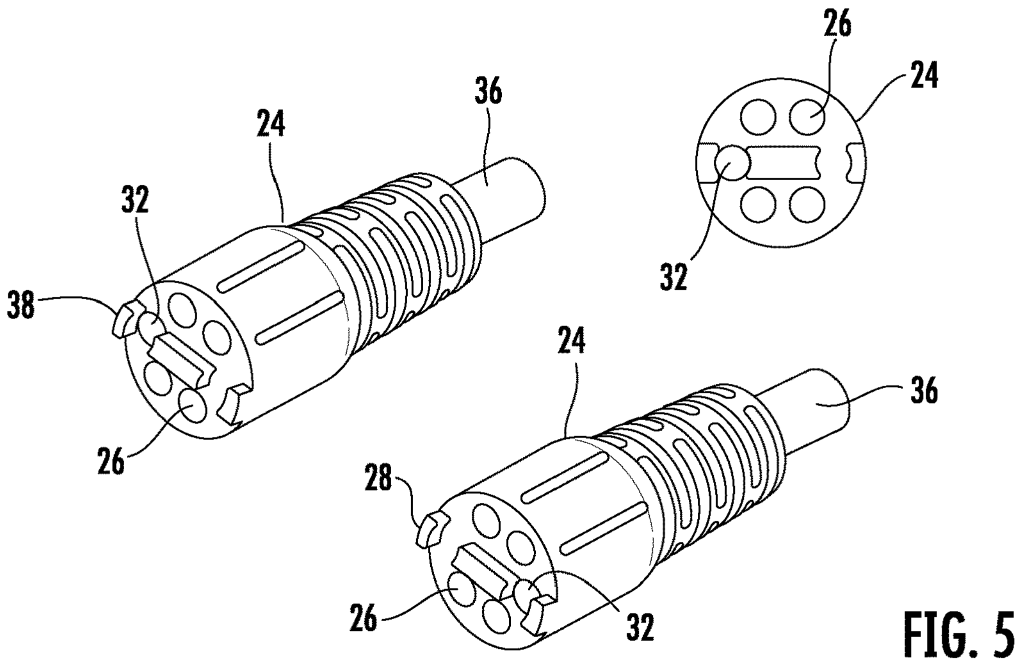
FIG. 5 shows various views of a lamp socket.

FIG. 5 shows opposing perspective views and an end view of the lamp socket 24. The lamp socket 24 is connected to a cable 36 which contains and shields wires that are disposed in communication with the connecting and detecting holes 26, 32 and extend through the cable 36 to be adjoined with the electrical power source.

Figure 6:
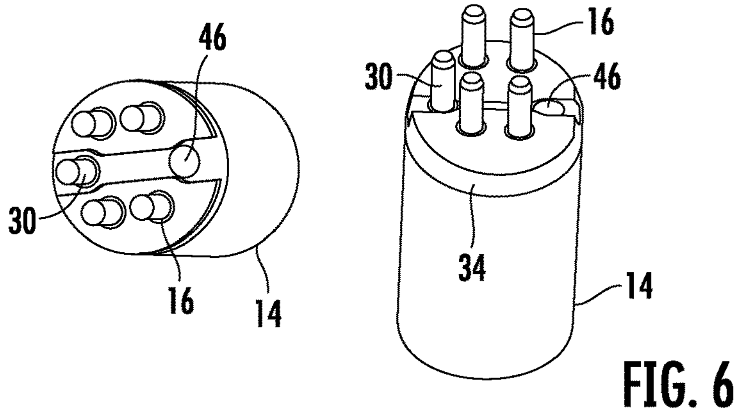
FIG. 6 shows various views of a lamp base.
Figure 7:
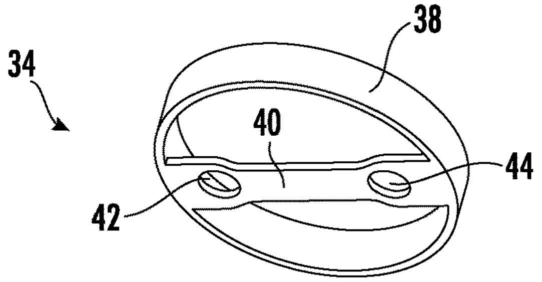
FIG. 7 shows a copper ring that, in one embodiment, is used in conjunction with a lamp base.

FIG. 6 shows perspective views of the lamp base 14. In this illustrative embodiment, the exposed portion 34 is comprised of a copper ring as shown in FIG. 7. The copper ring 34 includes an outer collar 38 having a circular shape and an interior member 40 which extends across a diameter of the outer collar 38. The interior member 40 includes a first hole 42 and a second hole 44. The copper ring 28 is fitted over the end of the lamp base 14 such that two of the connecting pins 16 extend through the outer collar 38 on one side of the interior member 40 and the other two connecting pins 16 extend through the collar 38 on the opposite side of the interior member 40. The detecting pin 30 passes through one of the first and second holes 42, 44, while a fixing member 46, such as a bolt or screw, passes through the other of the first and second holes 42, 44, in order to facilitate disposition of the copper ring 28 upon the lamp base 14.

The UV lamp 10 is powered by a first circuit 48 (see, FIG. 8) extending from the power source through the cable 36 to the connecting holes 26 of the lamp socket 24, through the mated connecting pins 16 of the lamp base 14, and to a filament disposed within the lamp tube 12.

A second circuit 50 is arranged within a ballast 52 to detect leakage of the charging current from the first circuit 48, which may occur due to the exposure of the system to water or moisture. The ballast 52 comprises the lamp base 14, the connecting pins 16, and related elements. The second circuit 50 is further configured to disable the first circuit 48 when a leakage charge threshold is reached. This second circuit 50 is composed of wiring which extends from a ballast through the cable 36 to the detecting hole 32 of the lamp socket 24 and through the mated detecting pin 30 to the copper ring 34.

During normal operation of the UV lamp 10, the second circuit 50 is electrically isolated from the first circuit 48. However, when a sufficient volume of water, moisture, or some other conductive fluid or substance contacts the detecting pin 30 and/or the exposed copper ring 34, the electrical isolation is bridged and charge passes from the first power circuit 48 to the second detecting circuit 50. This leakage charge is monitored by system, for example by the ballast, and when the leakage charge exceeds a certain value, the power supply to the UV lamp 10 is interrupted in order to avoid potential shock hazards.

Figure 8:
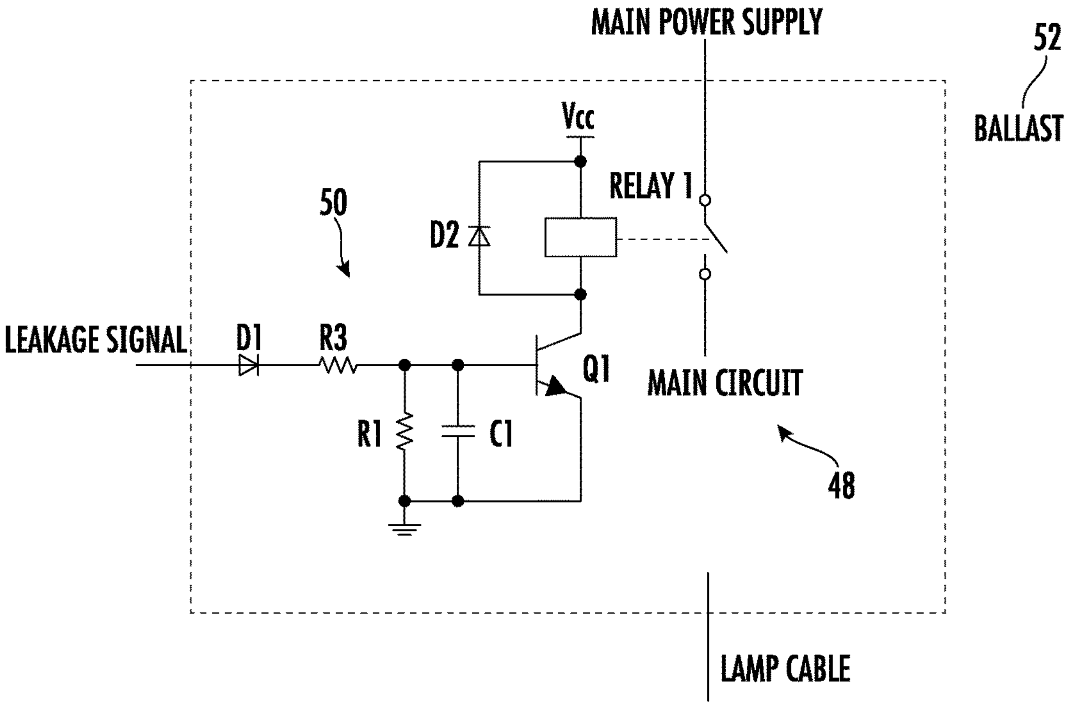
FIGS. 8-11 show various exemplary circuit arrangements for operating the UV lamp system in accordance with the invention.

FIG. 8 shows one exemplary embodiment of the first circuit 48 and the second circuit 50. As noted above, the ballast receives the detected leakage signal through the cable. The leakage signal is rectified to pulsating DC voltage by a diode D1. The DC voltage charges the capacitor C1 through the resistor R3. When the voltage of the capacitor C1 reaches the BE junction voltage of the transistor Q1, NPN transistor Q1 switches on. The transistor Q1 works in the saturation state. Then, a supply voltage Vcc is applied to a control end of a normally closed relay, Relay1, through the transistor Q1 CE junction. The output of the Relay1 opens and the main circuit power supply is cut off. The ballast has realized the leakage protection. Additionally, the ballast can be configured to generate sound alarm signals and/or light alarm signals according the leakage protection status.

Figure 9:
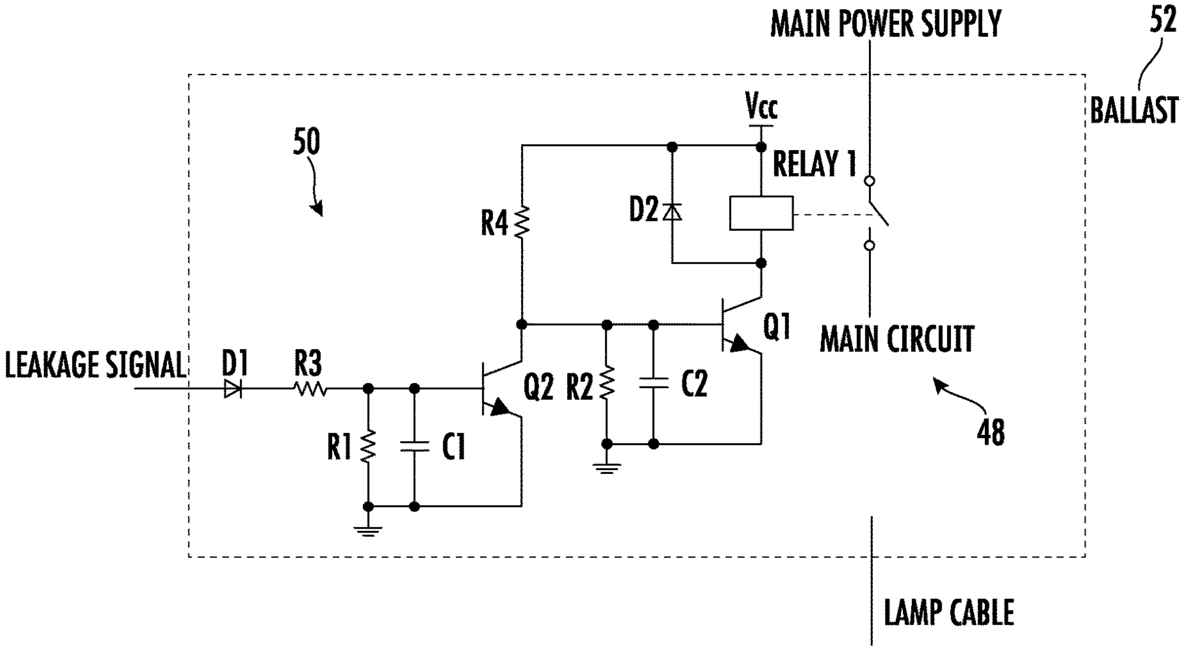

FIG. 9 shows an alternative exemplary embodiment of the first and second circuits. Here, the main circuit power supply is cut off by the normally opened relay, Relay1, when the ballast receives the detected leakage signal. That is, upon detection of the leakage signal, Relay1 is closed and the power supply is interrupted.

Figure 10:
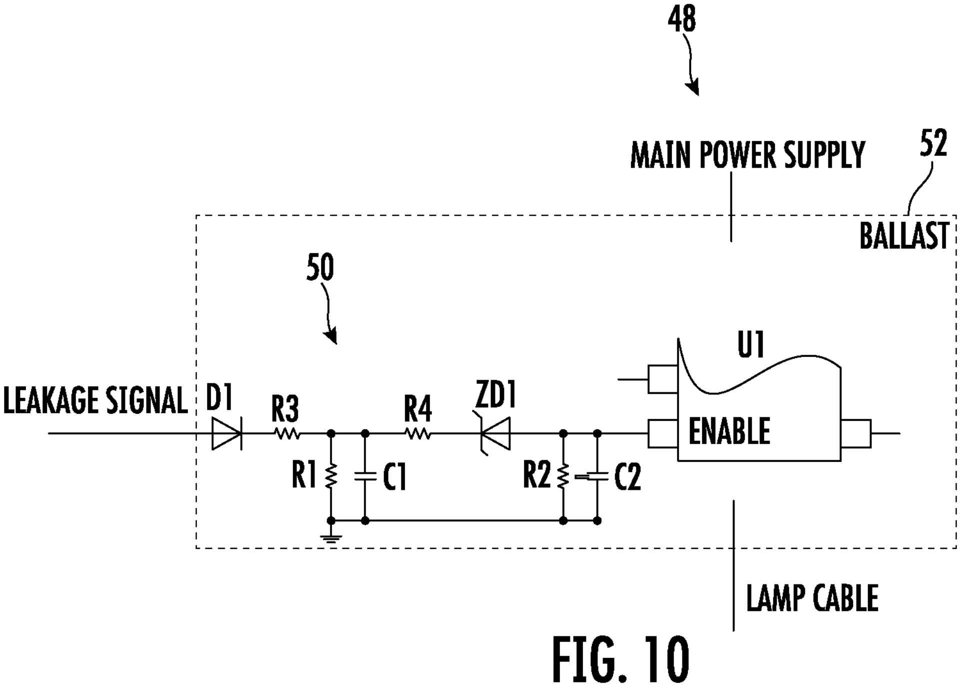

FIG. 10 shows a third alternative embodiment of the circuitry of the system. In this configuration, the ballast works in standby status through a chip disable or enable function when the ballast receives the detected leakage signal. The leakage signal is rectified to pulsating DC voltage by diode the D1. The DC voltage charges the capacitor C1 through the resistor R3. When the voltage of the capacitor C1 is above a Zener voltage of a zener diode ZD1, the ZD1 switches on. The C1 voltage charges the capacitor C2 through the resistor R4 and the Zener diode ZD1. When the voltage of the capacitor C2 reaches the disabled voltage of an ENABLE PIN in a chip U1, the chip has no output, and the ballast works in standby status. Accordingly, the ballast has realized the leakage protection.

Figure 11:
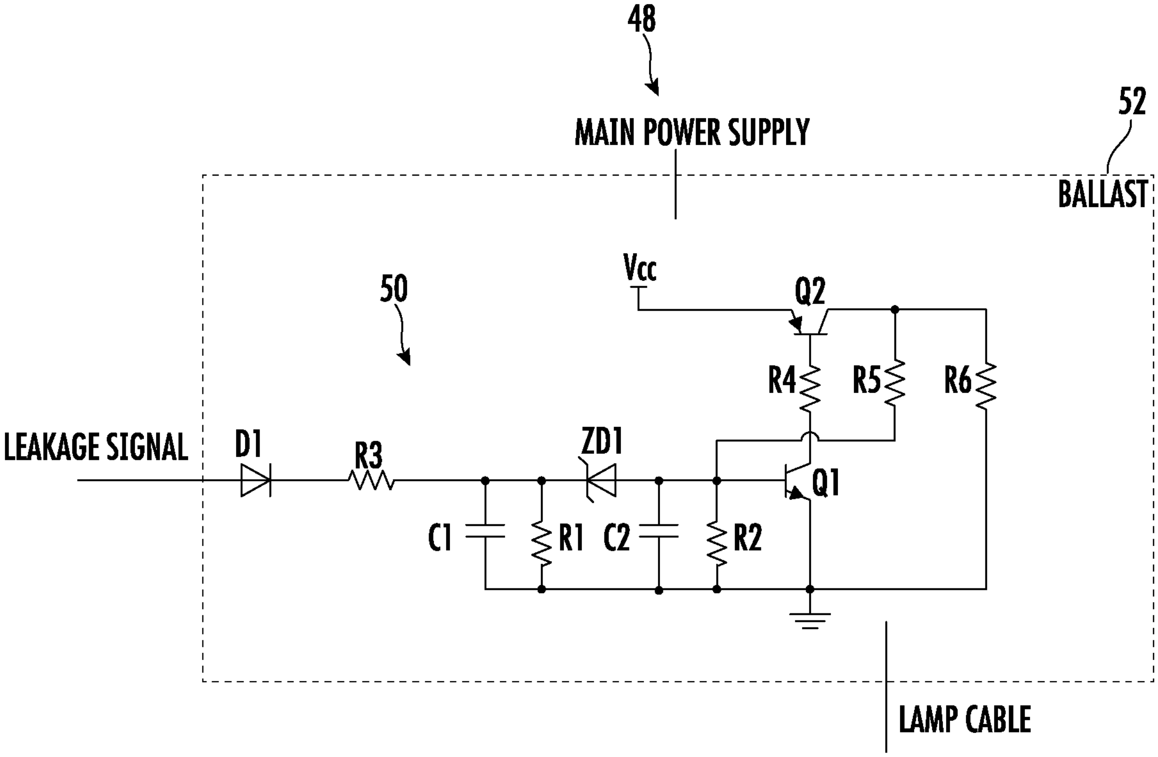

FIG. 11 shows yet another alternative embodiment of the electric circuit of the system. In this example, the ballast works in standby status through cutting off the control power supply Vcc when the ballast receives the detected leakage signal. The leakage signal is rectified to pulsating DC voltage by diode D1. The DC voltage charges the capacitor C1 through the resistor R3. When the voltage of the capacitor C1 is above the zener voltage of the zener diode ZD1, the ZD1 switches on. The C1 voltage charges the capacitor C2 through the Zener diode ZD1. When the voltage of the capacitor C2 reaches the BE junction voltage of the transistor Q1, the NPN transistor Q1 switches on. The transistor Q1 works in the saturation state, and the supply voltage Vcc can flow through the BE junction of the transistor Q2, the resistor R4 and the CE junction of the transistor Q1. Then the PNP transistor Q2 also switches on. The supply voltage Vcc is discharged through the CE junction of the transistor Q2 and the resistor R6. The control circuit stops work. At the same time, the supply voltage Vcc can flow through the CE junction of the transistor Q2, the resistor R5 and the resistor R2. And, it can maintain the supply voltage Vcc continuous discharge. In this way, the circuitry of FIG. 10 realizes the leakage protection described above.

The broad scope of the invention contemplates alternatives and variations in structure and circuitry which would preserve the functioning and advantages of the disclosed embodiments.

For example, while only a single detecting pin 30 was discussed above as being disposed upon the lamp base 14, an alternative embodiment may include additional such detecting pins 30, and, while shown as having a shape of a projecting cylinder, the pins 30 could have any feasible cross-sectional and/or projecting shape. The exposed portion 34 of the detecting pin is described in one embodiment as a copper ring. This portion 34 is optional and the lamp base 14 in an alternate embodiment may include the detecting pin 30 without the exposed portion 34. In still another embodiment, the exposed portion may be larger or smaller than that disclosed hereinabove and/or may be shaped differently, thus providing a different extent of exposure to liquid and moisture.

Where the lamp base includes a plurality of detecting pins 30, the respective lamp socket 24 has a corresponding number of detecting holes 32. Furthermore, each such additional detecting pin 30 and detecting hole 32 may include an additional wire extending internally therefrom to connect with the operating circuit, or such additional detecting pin 30 and detecting hole 32 may simply connect with a primary detecting pin 30 and detecting hole 32 in order to form a part of the operative circuit.

In similar manner, the number of connecting pins 16 on the lamp base 14 and the number of corresponding holes 26 in the lamp socket 24 may be increased or decreased as desired, and their shape, size, dimensions, and their material composition can be varied and modified.

Referring to FIG. 8, the circuit arrangement disclosed herein for operating the UV lamp 10 is configured essentially to power the lamp, to detect and process a leakage signal, and to cut off the main power supply when the leakage signal exceeds a set value by disrupting the normally closed relay. The diode D1, the transistor Q1 and the normally closed relay Relay1 are important factors. A current-limiting resistor R3 is incorporated along with a discharge resistor R1, damp diode/resistor D2 or filter capacitor C1. Of course an equivalent circuit may be used to replace these various parts, such as serial or parallel redundant components.

Referring to FIG. 9, the detected leakage signal is processed by the circuit, and when it exceeds the set value, the main circuit power supply circuit is cut off by manipulating the normally opened relay. The diode D1, the transistor Q1/Q2, the resistor R4 and the normally opened relay Relay1 are notable components of this circuit. For the circuit to work normally, additional components are provided: current-limiting resistor R3, discharge resistor R1/R2, damp diode/resistor D2 or filter capacitor C1/C2. Here again, it is possible to use the equivalent circuit to replace these various parts as desired, such as serial or parallel redundant components.

Referring to FIG. 10, the detected leakage signal is processed, and when it exceeds the set value, the main circuit is placed into a standby status by the disable or enable function of the chip. The set value is decided by the Zener voltage of the ZD1. The diode D1, the Zener ZD1 and the main control chip U1 are notable components of this circuit embodiment. For the circuit to work normally, additional components are provided: current-limiting resistor R3/R4, discharge resistor R1/R2 or filter capacitor C1/C2. As above, it is possible to use the equivalent circuit to replace these various parts as desired, such as serial or parallel redundant components.

In the embodiment of FIG. 11, the detected leakage signal is processed, and when it exceeds the set value, the main circuit work is placed into a standby status by cutting off Vcc in the control circuit. The set value is decided by the Zener voltage of the ZD1. Here, the he diode D1, the Zener ZD1, the resistor R6 and the transistor Q1/Q2 are essential to the circuit. The current-limiting resistor R3/R4, discharge resistor R1/R2, divider resistor R5 or filter capacitor C1/C2 are provide to support the primary components of the circuit. Once more, it is possible to use the equivalent circuit to replace these various parts as desired, such as serial or parallel redundant components.

Various embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship.

The term "exemplary" is used herein to mean "serving as an example, instance, or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. Terms such as "connected to", "affixed to", etc., can include both an indirect "connection" and a direct "connection."

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A water immersive electric shock protection apparatus for an ultraviolet (UV) sanitation system, the apparatus comprising:

a lamp base having a proximal end configured to be mounted to a tube of a UV lamp and a distal end having a plurality of connecting pins extending therefrom, the plurality of connecting pins arranged to deliver electrical power to the UV lamp;

a lamp socket having a plurality of connecting holes corresponding to the plurality of connecting pins and configured to receive said connecting pins, a first electrical circuit disposed in communication with the plurality of connecting holes and extending to and connectable with an electrical power source, the first electrical circuit arranged to deliver electrical power from the power source to the plurality of connecting pins when received in the corresponding plurality of connecting holes and when the electrical power source is turned on;

a detecting pin extending from the distal end of the lamp socket and including an exposed portion;

a detecting hole formed in the lamp socket, configured to receive the detecting pin when the plurality of connecting holes said receive the plurality of connecting pins, a second electrical circuit disposed in communication with the detecting hole which receives a leakage signal from the first electrical circuit when the exposed portion of the detecting pin is exposed to a volume of a conductive substance that bridges the first electrical circuit to the second electrical circuit;

a detecting device connected to the second electrical circuit and configured to detect the leakage signal, to compare the leakage signal to a predetermined set value, and to turn off the electrical power source when the leakage signal exceeds the predetermined set value.

2. The apparatus of claim 1, wherein the plurality of connecting pins comprise four cylindrically shaped pins extending from the distal end of the lamp base, and wherein the plurality of connecting holes comprise four cylindrically shaped holes extending into an interior of the lamp socket.

3. The apparatus of claim 1, wherein the detecting pin comprises a cylindrical element and the detecting hole comprises a cylindrical hole extending into an interior of the lamp socket.

4. The apparatus of claim 1, wherein the detecting pin comprises a plurality of cylindrical elements and the detecting hole comprises a corresponding plurality of cylindrical holes extending into an interior of the lamp socket.

5. The apparatus of claim 1, wherein the exposed portion of the detecting pin comprises a conductive area located on the distal end of the lamp base and connected electrically to the detecting pin.

6. The apparatus of claim 5, wherein the exposed portion comprises a ring formed of copper having an outer collar extending around the ring and an interior member bisecting the ring.

7. The apparatus of claim 6, wherein the interior member includes a hole through which a part of the detection pin passes when the ring is mounted on the distal end of the lamp base, the ring contacting the detecting pin at the hole to be said connected electrically to the detecting pin.

* * * * *